United States Patent [19]

Honig

[11] Patent Number: 4,915,630
[45] Date of Patent: Apr. 10, 1990

[54] DENTAL SPLINT

[76] Inventor: Gordon C. Honig, 737 Taunton Rd., Wilmington, Del. 19803

[21] Appl. No.: 351,939

[22] Filed: May 15, 1989

[51] Int. Cl.⁴ .................................................. A61C 5/00
[52] U.S. Cl. ........................................ 433/215; 433/9; 128/89 A
[58] Field of Search ................... 433/215, 1, 8, 9; 128/89 A

[56] References Cited

U.S. PATENT DOCUMENTS

| | | | |
|---|---|---|---|
| 3,337,957 | 8/1967 | Reed | 433/215 |
| 3,395,455 | 8/1968 | Overby et al. | 433/215 |
| 3,462,838 | 8/1969 | Alstergren | 433/1 |
| 3,675,327 | 7/1972 | Huget et al. | 433/215 |
| 4,470,809 | 9/1984 | Klepacki | 433/9 |
| 4,504,229 | 3/1985 | Garito et al. | 433/215 |
| 4,516,938 | 5/1985 | Hall | 433/215 |
| 4,533,320 | 8/1985 | Piekarsky | 433/9 |
| 4,557,692 | 12/1985 | Chorbajian | 433/215 |
| 4,609,350 | 9/1986 | Krause | 433/215 |
| 4,614,497 | 9/1986 | Kurz | 433/8 |

*Primary Examiner*—John J. Wilson
*Attorney, Agent, or Firm*—Connolly and Hutz

[57] ABSTRACT

A dental splint comprises a body member having a generally planar lower contact surface which establishes a bite plane. The body member is bonded to a single tooth along a side surface. A ligation wire is inserted through a hole extending through the body member to tie the splint to the tooth and to other splints.

10 Claims, 1 Drawing Sheet

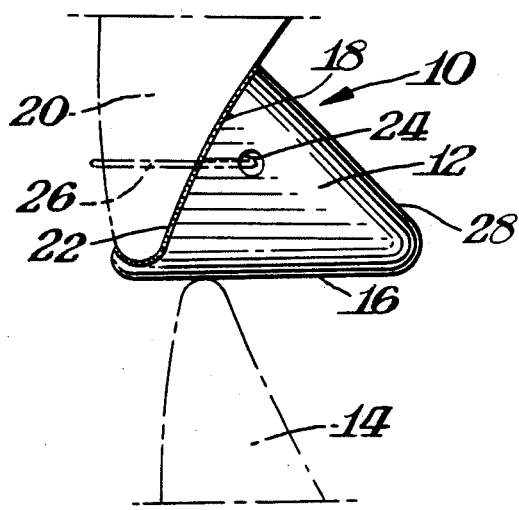
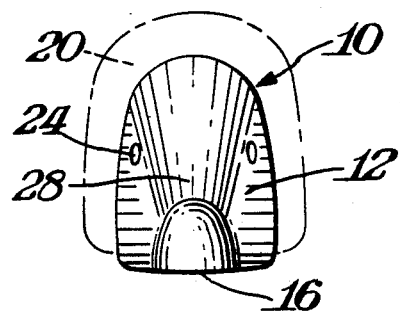
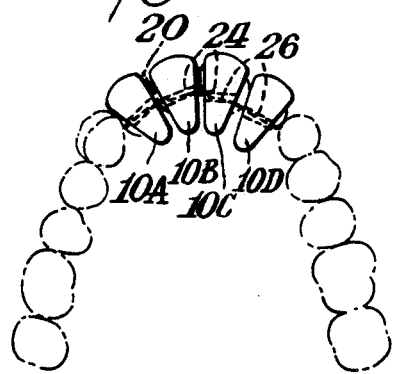
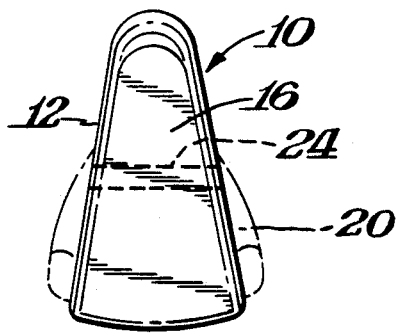

DENTAL SPLINT

BACKGROUND OF INVENTION

Splints are devices that are interposed between the upper and lower dental arches to affect a change in how the upper teeth meet the lower teeth. Splints are used in dentistry and orthodontics in the following ways:

to treat and diagnose problems of the temperomandibular (jaw) joints. Splints eliminate trauma to the joints caused by the bite (the way the teeth mesh) and allow the muscles of the jaws to relax and thereby relieve muscle tension and pain.

in orthodontics to help facilitate tooth movement. Splints are used to eliminate interferences that teeth from opposing arches cause during tooth movement, as well as interference caused by braces.

splints are also used in orthodontics to help in the correction of deep overbites (the vertical overlapping of the front teeth). They do this by allowing the extrusion of back molar teeth since when a splint is in place the back molar teeth are disarticulated (do not meet).

splints are also used to help protect teeth that have been weakened by periodontal (gum) disease.

In all cases, the types of splints now being used are of a type called removable appliances. These are devices that are fabricated to clip onto the teeth and that can be removed by the patient. They come in many different designs and employ different mechanisms for retention (holding them in place) and are made for either jaw. The need for retention necessitates much of the bulk of these devices.

The disadvantages with conventional dental splints are the following:

they require a two step procedure to be fabricated. This usually involves an impression (mold) be made of the teeth that it will be attached to and a laboratory procedure to make the splint which may take several hours to several weeks to be completed. A second visit is almost always necessary to deliver and place the splint.

virtually all splints are poorly tolerated by patients. They are usually very bulky and therefore interfere with speech and swallowing. They are uncomfortable to wear and can cause drooling. Patients also dislike them because they are often unsightly. They are also unpleasant since they cause a poor taste and smell. They must be removed for eating and cleaning which creates a nuisance especially since they can be lost. They are usually kept in a small case when not in use, which must be carried by the patient.

since these removable splints can be removed by the patients, their effectiveness is often reduced due to poor patient compliance.

once a mold is made of a particular dental arch to have a splint made, no further tooth movement can take place in that arch until splint use is discontinued. This often delays and complicates orthodontic treatment.

SUMMARY OF INVENTION

An object of this invention is to provide a splint which overcomes the disadvantages indicated above.

A further object of this invention is to provide such a splint which could be used with labial orthodontic appliances or could be used alone.

In accordance with this invention a splint comprises a body member having a generally planar lower contact surface which establishes the bite plane. The body member also includes a side surface which is bonded to a single tooth such as one of the maxillary central or lateral incisors. As many as four individual splints might be used on a patient. Each splint also includes a ligation wire hole extending completely through the body member so that a ligation wire could be inserted through the holes and around the corresponding teeth to tie the splints together in the event an individual splint should be inadvertently dislodged.

In a preferred embodiment of this invention the splint is completely made of a plastic material which is hard enough to resist defamation by occlusal forces and is made of small enough dimensions to permit individual tooth movement. Preferably, the body member has rounded contours to be compatible with the tongue or other oral soft tissue.

THE DRAWINGS

FIG. 1 is a side elevation view showing a splint in accordance with this invention mounted on an incisor;

FIG. 2 is a front elevation view of the splint shown in FIG. 1;

FIG. 3 is a bottom plan view of the splint shown in FIGS. 2-3; and

FIG. 4 is a bottom plan view of a plurality of splints mounted on maxillary incisors in accordance with this invention.

DETAILED DESCRIPTION

FIG. 1 illustrates a splint 10 in accordance with this invention. As shown therein the splint comprises a body member 12 made of a suitable plastic material as is known in the dental art which would be hard enough to resist deformation by occlusal forces, such as from lower incisor 14. In this respect, body member 12 includes a generally planar lower contact surface 16 in the path of motion of lower incisor 14 so as to limit the upward movement of lower incisor 14 past the general plane of the patient's bite.

Body member 12 also includes an upwardly extending front surface 18 which is anchored or bonded to the upper incisor 20 on its lingual side by means of a suitable dental adhesive 22. Splint 10 is intended to be permanently mounted to incisor 20 in the sense that it is intended to remain bonded to the incisor over a prolonged period of time. This differs from the general approach taken by the prior art where the larger size splints are readily detachably mounted.

A distinct difference of splint 10 from the splints of the prior art is its small size. In this respect, as indicated above splint 10 is dimensioned to be mounted to a single tooth and extends lingually only a sufficient distance so as to be in the path of motion of a corresponding lower incisor. In practice any suitable number of splints may be bonded to any corresponding number of teeth. The preferred practice of the invention, however, is to mount a splint to each of the four maxillary central and lateral incisors. Thus, FIG. 4 illustrates four such splints 10A, 10B, 10C and 10D mounted to the corresponding maxillary incisors.

Although it is intended to have the splints permanently mounted to the respective incisors, the invention takes into account the possibility that a splint might be inadvertently dislodged. Accordingly, body member 10 includes a ligation wire hole 24 extending completely through the body member so that a ligation wire 26 may be inserted through the hole and wrapped around the corresponding incisor 20 to act as a safeguard by tying the splint to the incisor. Where a plurality of splints are used, such as illustrated in FIG. 4, the preferred practice of the invention would be to use a single ligation wire extending through all of the holes 24 and then around all of the corresponding incisors. This has the added safeguard of not only tying a splint to its incisor, but also tying all of the splints together. Thus, if a splint should be inadvertently dislodged it will not fall into the mouth where it might be swallowed by the patient.

As illustrated, the shape of the splint body member 12 is such as to minimize its dimensions thereby permitting individual tooth movement. Additionally, body member 12 is of rounded contours so as to be compatible with the tongue and other oral soft tissue. Further, the shape and size of splint 10 is such as to allow for proper oral hygiene. Various thicknesses may be used to open bites differently. The lower contact surface 16 provides a flat surface for the lower incisor 14 to rest against during orthodontic treatment and thus established the bite plane. Splint 10, however, because of its small size could be used alone and it is not necessarily used with labial orthodontic appliances.

As shown, splint 10 is lingually bonded as an anterior splint and includes a generally triangularly shaped contact surface 16 (FIG. 3) as well as generally triangular shaped side walls which merge into each other along the top edge 28 of body member 12 as best illustrated in FIG. 2. Additionally, the anchoring front surface 18 is inclined so as to intimately conform to the lingual surface of its corresponding incisor 20. By having the individual splints of minimal size it is possible to separate the individual splints and thereby avoid possible aspiration. Moreover, different sized splints could be used for varying the depths of bite. A further advantage of the small size splint is that the lingual mounting results in the splints not being readily visible and thus, would be more acceptable to patients. Moreover, the splints permit the orthodontist to proceed with the treatment while leaving the splints bonded in place. The inclusion of the ligation wire 26 results in a safety device which prevents aspiration or swallowing of a splint.

The lingual bonded splint 10 overcomes all of the current disadvantages of the conventional removable varieties yet has few disadvantages. A summary of its advantages are the following:

The lingual bonded splint 10 does not require a two step procedure to be made. It can be placed in one visit in a short period of time.

The lingual bonded splint 10 is much more easily tolerated by patients. It is much less bulky and therefore is more comfortable, creates less speech interference, less drooling and is not visible to other people so that it is not unsightly. Splints 10 are cleaned like braces (in the mouth) and therefore are not removed for eating and cleaning requiring no carry along case.

The lingual bonded splint 10 is not removable and therefore is more effective in its action since variable patient use is eliminated.

Since the lingual bonded splint 10 is attached to individual teeth, orthodontic tooth movement can take place during splint use. This eliminates treatment delay and simplifies orthodontic procedures.

What is claimed is:

1. A dental splint for attachment to a tooth to establish a bite plane comprising a body member, said body member having a generally planar lower contact surface, an anchoring front surface extending upwardly and inwardly from said contact surface, and said anchoring surface being of a size and shape to fit snugly lingually against a single tooth and to be bonded to the tooth by application of an adhesive thereto.

2. The splint of claim 1 including a ligation wire hole extending through said body member whereby said splint may be tied to other splints by a wire extending through said hole and through other splints around corresponding teeth.

3. The splint of claim 2 wherein said body member is made of a plastic material and has rounded contours.

4. The splint of claim 3 wherein said contact surface is generally triangularly shaped.

5. The splint of claim 4 wherein said body member has an upper edge, said anchoring front surface sloping inwardly toward said upper edge, said body member having a pair of side surfaces, and said side surfaces being generally triangularly shaped and inclined toward each other and merging together at said upper edge.

6. The splint of claim 1, in combination therewith, a plurality of said splints, and said splints being tied together but spaced from each other by a ligation wire extending through said ligation wire holes.

7. In a method of establishing a bite plane, the improvement being in bonding a splint to the lingual side of a single maxillary tooth with the splint having a generally planar contact surface extending inwardly into the mouth to provide a bite plane for corresponding lower teeth moving toward the maxillary tooth.

8. The method of claim 7 including inserting a ligation wire through the splint, and securing the ligation wire to the upper tooth.

9. The method of claim 8 including bonding a plurality of splints to a corresponding number of maxillary teeth with the splints spaced from each other, and tying all of the splints together by the ligation wire.

10. The method of claim 9 wherein four splints are mounted to the maxillary central and lateral incisors.

* * * * *